United States Patent
Heimberg et al.

(10) Patent No.: US 6,656,724 B1
(45) Date of Patent: Dec. 2, 2003

(54) APPARATUS FOR AUTOMATIC IMPLEMENTATION OF CHEMICAL OR BIOLOGICAL METHODS

(75) Inventors: Wolfgang Heimberg, Ebersberg (DE); Michael Weichselgartner, Ebersberg (DE); Martin Greber, Ebersberg (DE); Peter Kutsch, Rosenheim (DE)

(73) Assignee: MWG-Biotech AG, Ebersberg (DE)

( * ) Notice: Subject to any disclaimer, the term of this patent is extended or adjusted under 35 U.S.C. 154(b) by 0 days.

(21) Appl. No.: 09/554,743

(22) PCT Filed: Nov. 19, 1998

(86) PCT No.: PCT/EP98/07423

§ 371 (c)(1),
(2), (4) Date: May 17, 2000

(87) PCT Pub. No.: WO99/26070

PCT Pub. Date: May 27, 1999

(30) Foreign Application Priority Data

Nov. 19, 1997 (DE) ..................... 297 20 432 U

(51) Int. Cl.[7] .............................................. C12M 1/36
(52) U.S. Cl. ................... 435/286.4; 435/287.2; 435/287.3; 435/303; 435/809; 422/65; 422/100; 422/104
(58) Field of Search ............... 435/286.1, 286.4, 435/286.5, 287.2, 288.3, 303.1, 809, 287.3; 422/99, 100, 104, 65, 63

(56) References Cited

U.S. PATENT DOCUMENTS

| | | | |
|---|---|---|---|
| 4,326,851 A | | 4/1982 | Bello et al. |
| 4,681,742 A | * | 7/1987 | Johnson et al. ............. 356/246 |
| 5,055,262 A | | 10/1991 | Sakagami |
| 5,096,670 A | * | 3/1992 | Harris et al. |
| 5,102,623 A | * | 4/1992 | Yamamoto et al. ......... 141/130 |
| 5,106,584 A | * | 4/1992 | Funakubo et al. |
| 5,122,342 A | * | 6/1992 | McCulloch et al. |
| 5,210,927 A | | 5/1993 | Lamont et al. |
| 5,443,791 A | | 8/1995 | Cathcart et al. ............. 422/65 |
| 5,474,744 A | | 12/1995 | Lerch |
| 5,492,831 A | | 2/1996 | Ranger |
| 5,496,517 A | * | 3/1996 | Pfost et al. ................. 422/100 |
| 5,529,754 A | | 6/1996 | Bonacina et al. |
| 5,580,524 A | * | 12/1996 | Forrest et al. ............. 366/213 |
| 5,639,425 A | * | 6/1997 | Komiyama et al. |
| 5,772,962 A | * | 6/1998 | Uchida et al. |
| 5,795,547 A | * | 8/1998 | Moser et al. |
| 5,846,489 A | | 12/1998 | Bienhaus et al. ............. 422/63 |
| 5,928,952 A | * | 7/1999 | Hutchins et al. ............ 422/104 |
| 6,044,212 A | * | 3/2000 | Flavin et al. |

FOREIGN PATENT DOCUMENTS

| | | |
|---|---|---|
| CA | 2130013 | 10/1993 |
| DE | 3841961 A1 | 6/1990 |
| DE | 4412286 A1 | 10/1995 |
| GB | 2196428 A | 4/1988 |

OTHER PUBLICATIONS

Copy of International Preliminary Examination Report for PCT/EP98/07423 dated Aug. 19, 1999.

(List continued on next page.)

Primary Examiner—William H. Beisner
(74) Attorney, Agent, or Firm—Rankin, Hill, Porter & Clark LLP

(57) ABSTRACT

The invention relates to a device for automatic implementation of chemical or biological methods in sample vessels, more particularly for sequencing and amplifying nucleic acid sequences, including a pipette apparatus and a thermocycler, the pipette apparatus comprising a pipette arm for pipetting sample substances and/or chemicals. The invention is characterized in that the pipette apparatus and the thermocycler are configured as spatially separated workstations and that a handling arm for moving at least one sample vessel containing sample substances or chemicals and configured separate from the workstations is provided.

11 Claims, 2 Drawing Sheets

OTHER PUBLICATIONS

Figure 1:
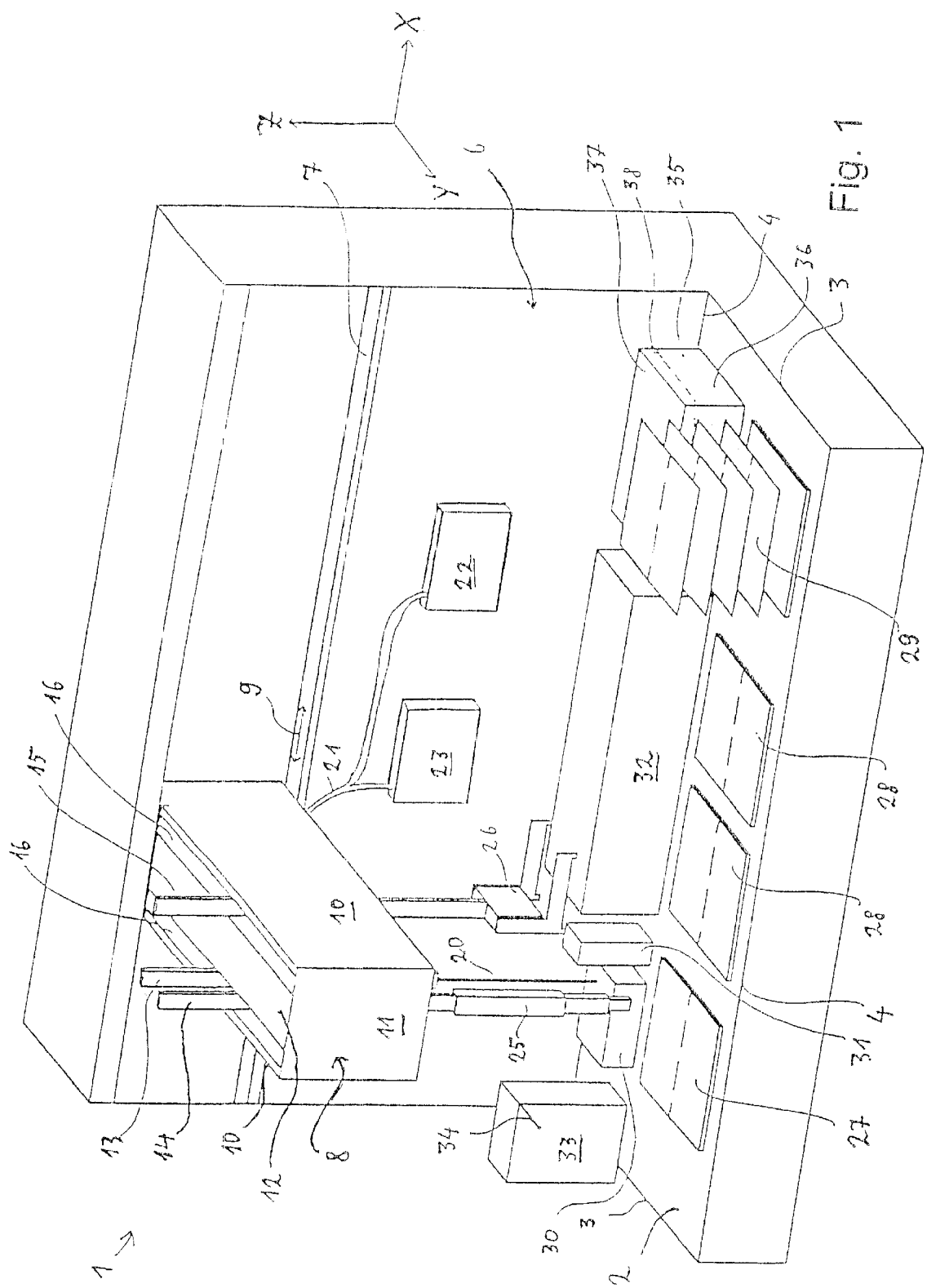

Blocker et al. "Methoden der Genomanalyse," GBF, Wissenschaftlicher Ergebnisbericht 1996, pp. 41–44.

Hawkins et al., "A Magnetic Attraction to High–Throughput Genomics," Science, vol. 276, Jun. 20, 1997, pp. 1887, 1889.

Brochure entitled The First Automated System for PCR testing, COBAS AMPLICOR, Roche Diagnostic Systems No date provided.

Didomenico et al., COBAS AMPLICOR(TM): fully automated RNA and DNA amplification and detection system for routine diagnostic PCR, Clinical Chemistry 42, No. 12, 1996, pp. 1915–1923.

Kost, M.D., Ph.D., "Handbook of Clinical Automation, Robotics, and Optimization," p. 9, No date provided.

Martin, "COBAS AMPLICOR (tm) Automatisation der AMPLICOR PCR," Roche Diagnostic TOP–News, Mar. 1995.

Caratsch, "COBAS T Instrument Concept," Tegimenta, Dec. 12, 1991, pp. 1–74.

* cited by examiner

APPARATUS FOR AUTOMATIC IMPLEMENTATION OF CHEMICAL OR BIOLOGICAL METHODS

The invention relates to a device for automatic implementation of chemical or biological methods, more particularly for sequencing and amplifying nucleic acid sequences, including a pipette apparatus and a thermocycler, the pipette apparatus comprising a pipette arm for pipetting sample substances and/or chemicals.

U.S. Pat. No. 5,443,791 discloses a device for implementing chemical or biological methods which comprises several workstations. These workstations are, among others, a thermocycler, an actively cooled enzyme storage station, a wash station, a reagent storage station and a DNA sample station. In this known device a pipette tip is moved in a plane parallel to the worksurface to implement a liquid transfer. The reaction vessels of this device are configured as dished cavities in a metal block arranged in the thermocycler. The individual reagents are first pipetted in one of the reaction vessels located in the thermocycler and then subjected to a temperature profile. Before a further reaction can be carried out the reaction vessel(s) need to be cleaned. Should cleaning fail to be total, subsequent reactions are contaminated which in highly sensitive methods such as the PCR method is a very serious drawback. In addition to this it is of disadvantage that the reaction vessels are configured as dished cavities in a metal block which come into direct contact with the reagents. Metal surfaces cannot always be cleaned totally free of any remainders at reasonable expense and thus form a further source of contamination.

Using thermocyclers enables predetermined temperature profiles to be instrumented. Thermocyclers are used more particularly in gene technology for sequencing and amplifying nucleic acid sequences. Such methods are described e.g. in EP 200 362 B1, EP 258 017 B1 and EP 201 184 B1.

Known from DE 44 12 286 A1 is a system for closing off samples vessels by means of covers. This system comprises a means for opening and closing reaction vessels able to grip and relocate a cover by means of a latching mechanism.

The invention is based on the object of sophisticating a device of the aforementioned kind such that it is suitable for automatic implementation of chemical or biological methods, more particularly for sequencing and amplifying nucleic acid sequences with no contamination.

This object is achieved by a device having the features of claim 1. Advantageous aspects read from the sub-claims.

The invention is characterized in that the pipette apparatus and the thermocycler are configured as spatially separated workstations and that a handling arm for moving at least one sample vessel containing sample substances or chemicals and configured separate from the workstations is provided.

Spatially separating the pipette apparatus and thermocycler and providing reaction vessels configured independent of the workstations, whereby the reaction vessels are moved by a handling arm between the individual workstations, permits fully automated implementation of complex chemical and biological methods with a high thruput since reaction vessels are simultaneously located in the pipette apparatus and in the thermocycler and correspondingly worked without necessitating any complicated cleaning procedures on the device. This enables complex methods working more particularly with totally different reagents and sample substances to be implemented fully automated practically simultaneously and/or in sequence.

The device in accordance with the invention thus enables complex chemical and biological methods, more particularly sequencing and amplifying nucleic acid sequences to be implemented fully automated and free of contamination. Thus greatly simplifying and significantly enhancing accuracy and safety in the working procedures.

The embodiment as it reads from claim 3 including a multi-tasking controller permits robotic handling of various sample substances, applications etc simultaneously without a laboratory worker being needed for monitoring and checking the individual steps in the process, as a result of which, even the most complex method profiles can now be implemented in a minimum space environment with no risk of error due to mistakes in siting or the like.

A further preferred embodiment of the device in accordance with the invention comprises a means for automatically opening and closing sample vessels by means of covers. It is usual in automated devices that the sample vessel is closed off by a film of wax or oil. Closing it off in this way is popular in manual implementation of chemical or biological reactions. Making use of covers releasably secured to the vessels has salient benefits in automated operation as compared to the conventional use of wax or oil films. Thus, a vessel once filled with reagents and/or sample substances and closed off with a cover can be reopened and additional reagents and sample substances added. The reagents and sample substances are introduced into the reaction vessel by means of a pipette tip held just above the liquid surface in the reaction vessel so that there no contact between the pipette tip and the reagents and sample substances contained in the reaction vessel to thus reliably prevent cross-contamination by the transfer of reagents and sample substances from one reaction vessel to the other.

In conventionally sealing the reaction vessels the pipette tip needs to penetrate the wax or oil film during pipetting and to dip into the liquid contained in the reaction vessel. Before applying the pipette tip to a further reaction vessel e.g. the same substance, the pipette tip needs to be cleaned or replaced. This is usual in manual implementation of chemical and biological reactions, it adding to the time and costs needed in implementing the reactions fully automated.

When movements occur in the liquid contained in the reaction vessel or movements of the reaction vessel itself or delayed boiling during a heating phase in the thermocycler such an oil or wax film cannot reliably prevent liquid from escaping from the reaction vessel and e.g. slosh-contaminating a neighboring reaction vessel.

In addition to this, sealing with wax has the disadvantage that this solidifies when cooled to low temperatures (e.g. 14° C.) and obstructs further treatment.

Figures 2, 3:
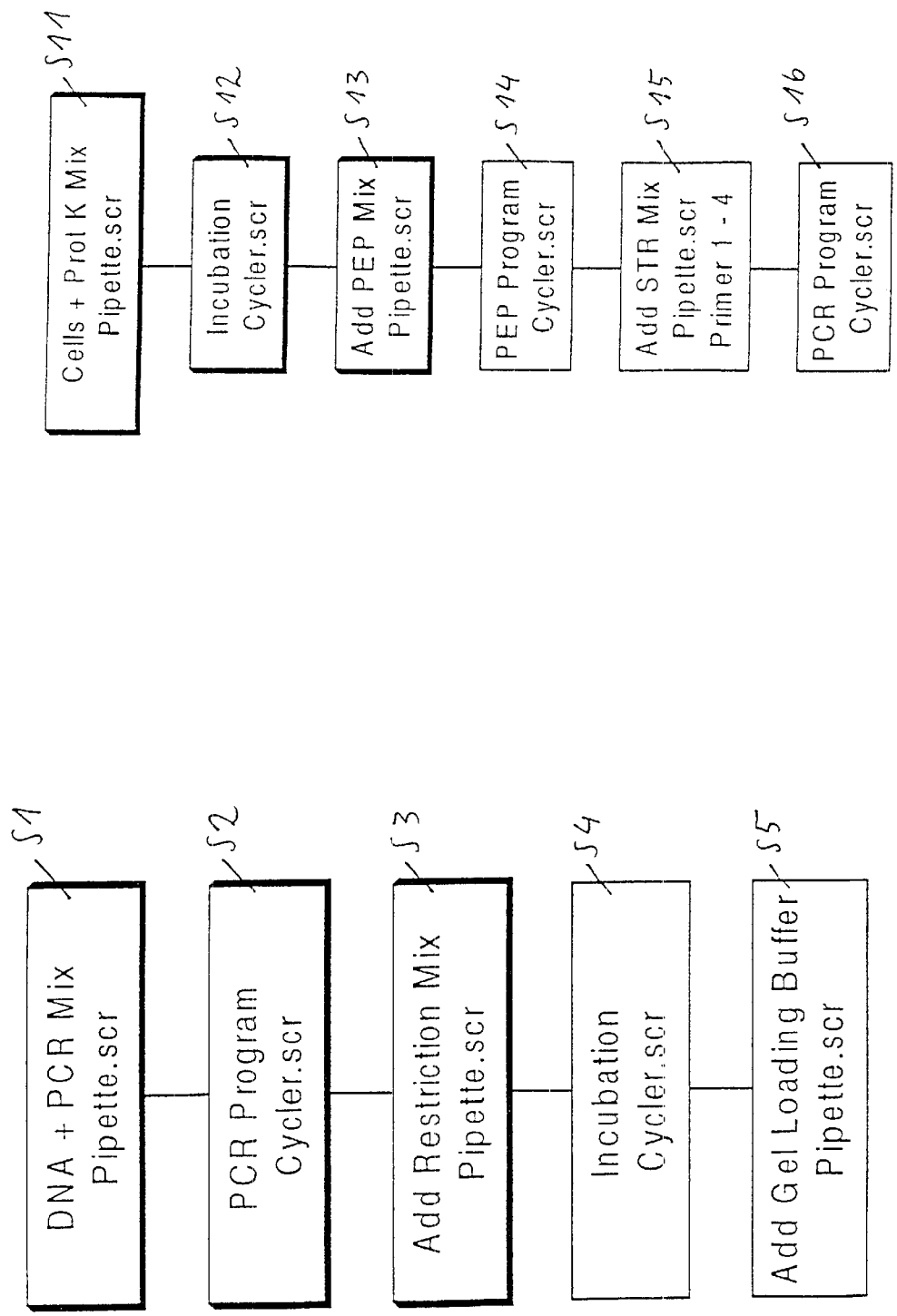

The invention will now be detained by way of an example with reference to the attached drawings in which FIG. 1 is a schematic view in perspective of one example embodiment of a device in accordance with the invention FIG. 2 is a flow diagram for one typical application, and FIG. 3 is a flow diagram for another typical application.

Referring now to FIG. 1 there is illustrated the device 1 in accordance with the invention comprising a rectangular worksurface 2 having two face edges 2 and a front and rear longitudinal edge 4. Arranged on the worksurface 2 at its rear longitudinal edge 4 is a rear wall 6. Provided at the upper edge portion in the rear wall 6 is a horizontal rail 7 running parallel to the rear longitudinal edge 4 of the worksurface 2. Mounted travelling on the rail 7 in the longitudinal direction thereof (double-arrow 9, X direction) is a robotic arm 8.

The robotic arm 8 is arranged straight and rigid parallel to the face edges 3 of the worksurface 2, it thus standing perpendicular to the plane of the rear wall 6. The robotic arm 8 is outwardly defined by comprising two longitudinal walls 10 and a face wall 11 at its free end, the face wall being arranged U-shaped as viewed from above. Disposed between the two longitudinal walls 10 and spaced away therefrom is a rail 12. Mounted travelling on the rail 12 in the longitudinal direction thereof (Y direction) are three Z arms 13–15. Each of the three Z arms 13–15 extends vertically through a gap 16 between the rail 12 and the longitudinal side walls 10, two of the Z arms 13, 14 being arranged in the gap 16 or the like and the third Z arm 15 being arranged in the gap 16 on the right.

The robotic arm 8 is powered to travel along the rail 7 (X direction) and the Z arms 13 along (Y direction) and perpendicular (Z direction) to the rail 12 so that the Z arms 13–15 can cover substantially the complete area (X direction, Y direction) above the worksurface 2 and are height-adjustable (Z direction).

The Z arm 13, termed pipette arm 13 in the following, comprises at its lower end an element for mounting a pipette tip 20 (indicated only schematically). The pipette tip is connected via a thin tube 21 to two pumps 22, 23. The pump 22 is a syringe pump for precise microdispensing (1 $\mu$l) whereas the second pump 23 is a wash pump having a greater thruput (e.g. $\geqq$100 ml/min) than the syringe pump 22 and is used for washing the pipette tip 20.

The Z arm 14, termed cover actuating arm 14 in the following, is provided at its lower end with a means 25 for automatically opening and closing the vessels as is known from DE 44 12 286 A1 and EP 734 769 A1. By means of a latching mechanism the means 25 is able to pick and release a cover.

When there is a risk of contamination each of the vessels containing the sample substances and chemicals may be provided with a cover which is automatically removed and refitted by the cover actuating arm 14. These closable vessels are put to use more particularly in the PCR method. In sequencing, the risk of contamination is less, this being the reason why making use of of such closable vessels is not a mandatory requirement.

The third Z arm 15 is termed handling arm 15 in the following. It comprises at its lower end a forked holding means 26 with which—similar to the action of a fork-lift truck—pipette plates (not shown) are lifted, moved and returned in place. Configured in the pipette plates is a plurality of sample vessels arranged in a rectangular grid pattern each closable with a cover. These pipette plates are locatable on the worksurface 2 as required by means of the handling arm 15.

Arranged on the worksurface 2 are a sample mount 27 and two pipette mounts 28. The sample mount 27 and the pipette mounts 28 are mounting fixtures configured identical on which the pipette plates are simply placed. The pipette plates placed on the mounting fixtures 27, 28 are thereby precisely registered relative to the worksurface 2 so that the site of each vessel configured in the pipette plates is precisely defined and can thus be located precisely by the robotic arm 8, more particularly the pipette arm 13 and the cover actuating arm 14. The pipette mounts 28 define pipette stations at which pipetting is implemented.

The mounts 27, 28 are arranged at the front longitudinal edge 4 of the worksurface 2 to facilitate placement of pipette plates thereon by the laboratory worker. Provided alongside the mounts 27, 28 is a stacker 29 configured as a miniature buffer storage/retrieval system for several, e.g. 5–10 pipette plates.

Provided in the rear portion of the worksurface 2 are a chemicals reservoir 30, a wash station 31, a pipette tip magazine 32 for disposable pipette tips and a pipette tip sweeper 33 for sweeping the disposable pipette tips. The disposable pipette tips are arranged vertically in the pipette tip magazine 32 so that the pipette arm 13 simply by lowering its lower end thereinto picks a disposable pipette tip which after use is swept away by the pipette tip sweeper 33.

Arranged on the pipette tip sweeper is a horizontally protruding pointer 34 of an electrically conductive and flexible material. The disposable pipette tips used are made of a conductive material such as e.g. a plastic incorporating graphite.

After being picked a new disposable pipette tip is brought into contact with or near to the pointer 34 by its edge portion adjoining the pipette arm 13. The pointer 34 is connected to a sensing means which senses a capacitance, from the result of which the system can "see" whether a disposable pipette tip is present in the pipette apparatus or whether picking the disposable pipette tip has malfunctioned. Accordingly, by means of the pointer and the sensing means, picking a new disposable pipette tip is checked. One substantial advantage of this checking means is that the disposable pipette tip does not need to be brought into contact with some object by its tip, as is known in conventional checking, but instead checking picking of the disposable pipette tips can now be done absolutely free of contamination.

When employing a reusable pipette this can be inserted as required in the wash station 31 between the individual pipetting actions and cleaned by being flushed out profusely with water by means of the wash pump 23.

Arranged in the chemicals reservoir 30 is a plurality of the vessels open at the top and holding various chemicals. The vessels of the chemicals reservoir 30 may be closed off by means of covers removed and refitted by means of the cover actuating arm 14.

In accordance with the invention a thermocycler tank 35 is arranged on the worksurface 2. The thermocycler tank 35 consists of a basebody 36 open at top which may be closed off by means of a cover 37. The cover 37 is secured to the basebody 36 by a hinge 38 about which it is swivelled by means of a motor (not shown) for automatically opening and closing the thermocycler tank 35. Provided in the thermocycler tank 35 are heating and cooling elements enabling the interior to be set to a specific temperature. It is also possible by means of the heating and cooling elements to configure specific temperature profiles. A Peltier element is used preferably as the heating and cooling element which is capable of both removing and supplying heat. A typical temperature range of one such thermocycler is −5° C. to 120° C. and the temperature can be varied at a heating/cooling rate of 2° C./s to 5° C./s.

The device in accordance with the invention comprises a central controller for controlling both the movement of the robotic arm 8 with its Z arms 13 to 16 as well as the individual function elements such as e.g. the pumps 22, 23 and the integrated thermocycler. This controller is arranged in the rear wall 6. However, it may also be accommodated in a separate housing or be represented by a separate component. The controller is preferably a processor-controlled device and configured as a multi-tasking controller, i.e. capable of implementing and monitoring several control actions at the same time.

The controller is provided with an interface to a computer. Stored in the computer are several data bases containing the data for the individual applications, sample management, chemicals and cycler programs. All the user needs to do is to insert a sample to be analyzed or processed, enter the type of application (sequencing, amplifying, etc), select the chemicals and cycler program, should the latter data (chemicals, cycler program) not already be stipulated by the application, and locate the sample on the sample mount 27.

The device in accordance with the invention then opens by means of the cover actuating arm 14 the vessels containing the sample substances and chemicals, transfers parts of the sample substances into the reaction vessels of the pipette plates arranged on the pipette mounts 28 and brings the sample substances into contact with the corresponding chemicals from the chemicals reservoir 30. During pipetting the pipette tips are preferably held just above the liquid surface in the reaction vessel to prevent transfer of reagents and sample substances from one reaction vessel to the other. This is particularly of advantage when the same substance is to be applied to several reaction vessels of a pipette plate, since this can now be quickly done without needing to clean the pipette tip between individual pipetting actions.

After pipetting, the pipette plates are inserted by the handling arm 15 either directly into the thermocycler tank 35 or buffered in the stacker 29 and supplied to the thermocycler tank 35 at some suitable later point in time.

Whilst a sample is subjected to a specific temperature profile in the thermocycler tank 35 a further sample may also be pipetted with other sample substances and another application.

Referring now to FIG. 2 there is illustrated a flow diagram of a typical, simple application of the device in accordance with the invention for amplifying a DNA sample. In this application a DNA sample is to be amplified before then being split specific in sequence and prepared for electrophoretic analysis.

For this purpose the laboratory worker selects from a menu display of the computer the sample substances, a predetermined mix of enzymes suitable for amplifying, a further predetermined mix for the sequence-specific splitting the amplifyied DNA sample and a gel as well as a buffer solution for preparing the electrophoretic analysis.

The computer then automatically produces the so-called pipetting and thermocycler scripts (pipette.scr and cycler.scr) as dictated by the defined sample substances and reagents. These scripts contain all control instructions needed for filling the reaction vessels and for incubation, including the transport instructions for moving the pipette plates and the instructions for opening and closing the covers. The thermocycler scripts also contain the temperature profile to be implemented in the thermocycler which may be modified manually, if required.

During a first working step S1 a pipette script is implemented, as a result of which the vessels of a pipette plate are filled with the selected sample substances and reagents and then the pipette plate supplied to the thermocycler.

In a second step S2 a temperature profile is instrumented in the thermocycler to amplify the DNA sample in accordance with a PCR method known as such. On completion of the amplification procedure the pipette plate is moved to a pipette mount.

In step S3 a further pipette script is implemented, the reaction vessels receiving a predetermined mix of restriction enzymes. The pipette plate is then retransported to the thermocycler and inserted therein.

In the next step S4 the DNA samples are split sequence-specific by they being subjected e.g. for 2 hours to a temperature of 37$_i$C. at which the restriction enzymes are particularly active. After this, the temperature is briefly increased to e.g. 95$_i$C. resulting in the restriction enzymes being deactivated. On completion of splitting of the DNA samples the pipette plate is returned to one of the pipette mounts 28.

step S5 gel and a buffer solution are added to the reaction vessels in preparation for a electrophoretic analysis.

The pipette plate together with the conditioned DNA sequences can then be removed by the laboratory worker or automatically buffered in the stacker 29.

Referring now to FIG. 3 there is illustrated the flow diagram of another method which can be implemented fully automatically by the device in accordance with the invention, this method serving to determine the length polymorphisms in DNA portions as is described, for example, in patent EP 438 512 B1 (=U.S. Pat. No. 5,766, 847).

The sample substances comprises in this arrangement complete cells which are lysed by means of a proteinase K in the steps S11 and S12.

In step S13 a mix of random primers—primer extension protocol (PEP)—is added and in step S14 amplified in accordance with the PCR method.

After this, in step S15 a mix of several primers and enzymes is added to detect simple or cryptic simple repeats of DNA sequences—short tandem repeats (STR)—before the corresponding PCR method is implemented (step S16).

It is to be noted that the methods or applications illustrated in FIGS. 2 and 3 are merely two examples of a wealth of possible applications of the device in accordance with the invention. Several of these applications are preprogrammed in the controller. However, the laboratory worker may also compose his own applications with a optional sequence of pipette and thermocycler scipts. The methods may be optionally complicated and e.g. involve circumscribing RNAs on DNAs, however, they are performed fully automated, according to the invention.

Various applications may be performed simultaneously and/or sequentially fully automated, without the laboratory worker having to monitor the individual steps. It is also possible to run an application in the thermocycler and another application in the pipette apparatus simultaneously. For this the control device is equipped with an additional function, which starts the pipetting process, which is in general quicker, in such a manner that it ends at the same time as the incubation running in the thermocycler. The mixture prepared during the pipetting process is added to the thermocycler without standing time, whereby undesired reactions are avoided.

With the invention a method is created which enables complete automated processing of complex chemical and/or biological methods, especially PCR-methods, where maximum flexibility referring to the kind of used method is reached. With this even the most complex method profiles can be implemented in a minimum of space environment with no risk of error due to mistakes in siting or the like. Most complex chemical and/biological methods, more particularly sequencing and amplifying nucleic acid sequences can be performed fully automated and with high efficiency and high thruput.

What is claimed is:

1. A device for implementing a chemical or biological method in a sample vessel supported by a pipette plate, and for sequencing and amplifying nucleic acid sequences, comprising:

a thermocycler disposed on a single worksurface, said thermocycler being operable to receive said pipette plate, and to affect the temperature of said sample vessel;

a pipette station that is disposed on said worksurface and is spatially separated from said thermocycler; and a robotic arm having a pipette arm and a handling device, said pipette arm being operable to pipette a sample substance into said sample vessel, and said handling device being operable to grip and release the pipette plate and to transport said pipette plate to and from said pipette station and said thermocycler.

2. The device as defined in claim 1, wherein said pipette arm has a lower end, configured to receive a disposable pipette tip, and said pipette arm communicates said pipette tip with a plurality of pumps via corresponding tubes, said plurality of pumps includes a fine metering pump and a wash pump, the wash pump having a throughput higher than a throughput of said fine metering pump for flushing said pipette tip, and said device further comprising a pipette tip magazine for supplying said disposable pipette tips and a pipette tip sweeper for sweeping said disposable pipette tips, both said magazine and said sweeper being disposed on said worksurface, and said magazine being operable to supply said disposable pipette tip for connection to said lower end of said pipette arm, and said sweeper being operable to sweep and dispose of said disposable pipette tip after use.

3. The device as defined in claim 2, further comprising an electrically-conductive, freely-protruding pointer and a sensor, said pointer and said sensor together being mounted on said pipette tip magazine and being operable to check whether said pipette tip is properly arranged on said pipette arm.

4. The device as defined in claim 11, further comprising a multitasking controller that is operative to control said pipette arm, said handling device and said thermocycler, whereby said controller controls said pipette arm to pipette material into said sampling vessel, said handling device to grip or release said pipette plate and transport said pipette plate to and from predetermined locations on the worksurface, and said thermocycler to subject said sample vessel to a predetermine temperature profile.

5. The device as defined in claim 1, wherein said sample vessel includes a cover, and said pipette arm comprises a cover actuating arm that is operative to open and to close said sample vessels cover.

6. A device for implementing a chemical or biological method in a sample vessel that is supported by a pipette plate and for sequencing and amplifying nucleic acid sequences, comprising:

a thermocycler disposed on a single worksurface, said thermocycler being operable to receive said pipette plate, and to affect the temperature of said sample vessel;

a pipette station that is disposed on said worksurface and is spatially separated from said thermocycler; and a handling system comprising a single rail, which is disposed adjacent to said worksurface and extends generally parallel with a plane defined by said worksurface, and a pipette arm and a handling device supported by said rail, said pipette arm being operable to pipette a sample substance into said sample vessel, and said handling device being operable to grip and release the pipette plate, said pipette arm and said handling device being further operable to move along said rail, whereby said sample vessel is filled with said sample material and transported in said pipette plate to and from said pipette station and said thermocycler by said handling system.

7. The device as defined in claim 6, wherein said pipette arm has a lower end configured to receive a disposable pipette tip, and said pipette arm communicates said pipette tip with a plurality of pumps via corresponding tubes, said plurality of pumps includes a fine metering pump and a wash pump, the wash pump having a throughput higher than a throughput of said fine metering pump for flushing said pipette tip.

8. The device as defined in claim 7, further comprising a pipette tip magazine for supplying said disposable pipette tip and a pipette tip sweeper for sweeping said disposable pipette tip, both said magazine and said sweeper being disposed on said worksurface, and said magazine being operable to supply said disposable pipette tip for connection to said lower end of said pipette arm, and said sweeper being operable to sweep and dispose of said disposable pipette tip after use.

9. The device as defined in claim 8, further comprising an electrically-conductive, freely-protruding pointer and a sensor, said pointer and said sensor together being mounted on said pipette tip magazine and being operable to check whether said pipette tip is properly arranged on said pipette arm lower end.

10. The device as defined in claim 6, wherein said sample vessel includes a cover, and said pipette arm comprises a cover actuating arm that is operative to open and to close said sample vessel cover.

11. The device as defined in claim 6, further comprising a multitasking controller that is operative to control said pipette arm, said handling device and said thermocycler, whereby said controller controls said pipette arm to pipette material into said sampling vessel, said handling device to grip or release said pipette plate and transport said pipette plate to and from predetermined locations on the worksurface, and said thermocycler to subject said sample vessel to a predetermine temperature profile.

* * * * *

UNITED STATES PATENT AND TRADEMARK OFFICE
CERTIFICATE OF CORRECTION

PATENT NO.     : 6,656,724 B1                                        Page 1 of 1
DATED          : December 2, 2003
INVENTOR(S)    : Heimberg, Wolfgang et al.

It is certified that error appears in the above-identified patent and that said Letters Patent is hereby corrected as shown below:

<u>Column,</u>
Line 30, Claim 4 should read:
4. The device as defined in claim 1, further comprising a multitasking controller that is operative to control said pipette arm, said handling device and said thermocycler, whereby said controller controls said pipette arm to pipette material into said sampling vessel, said handling device to grip or release said pipette plate and transport said pipette plate to and from predetermined locations on the worksurface, and said thermocycler to subject said sample vessel to a predetermine temperature profile.
Line 39, Claim 5 shoud read:
5. The device as defined in claim 1, wherein said sample vessel includes a cover, and said pipette arm comprises a cover actuating arm that is operative to open and to close said sample vessel cover.

Signed and Sealed this

First Day of June, 2004

JON W. DUDAS
*Acting Director of the United States Patent and Trademark Office*